(12) United States Patent
Goto et al.

(10) Patent No.: US 10,870,833 B2
(45) Date of Patent: Dec. 22, 2020

(54) METHOD FOR SEPARATING CELL FROM BIOLOGICAL TISSUE

(71) Applicants: Tohoku University, Sendai (JP); Meiji Seika Pharma Co., Ltd., Tokyo (JP); National University Corporation Tokyo University of Agriculture and Technology, Fuchu (JP)

(72) Inventors: Masafumi Goto, Sendai (JP); Kazutaka Murayama, Sendai (JP); Youhei Yamagata, Fuchu (JP); Kimiko Watanabe, Sendai (JP)

(73) Assignees: TOHOKU UNIVERSITY, Miyagi (JP); MEUI SEIKA PHARMA CO., LTD., Tokyo (JP); NATIONAL UNIVERSITY CORPORATION TOKYO UNIVERSITY OF AGRICULTURE AND TECHNOLOGY, Tokyo (JP)

( * ) Notice: Subject to any disclaimer, the term of this patent is extended or adjusted under 35 U.S.C. 154(b) by 0 days.

(21) Appl. No.: 16/109,242

(22) Filed: Aug. 22, 2018

(65) Prior Publication Data

US 2018/0362934 A1 Dec. 20, 2018

Related U.S. Application Data

(63) Continuation of application No. 14/765,020, filed as application No. PCT/JP2014/000527 on Jan. 31, 2014, now abandoned.

(30) Foreign Application Priority Data

Feb. 1, 2013 (JP) ................................ 2013-018774

(51) Int. Cl.
*C12N 5/071* (2010.01)
*C12N 5/00* (2006.01)

(52) U.S. Cl.
CPC ............. *C12N 5/0676* (2013.01); *C12N 5/00* (2013.01); *C12N 5/067* (2013.01); *C12N 2509/00* (2013.01)

(58) Field of Classification Search
CPC ........ C12N 5/0676; C12N 5/00; C12N 5/067; C12N 2509/00
USPC ...................................................... 435/381
See application file for complete search history.

(56) References Cited

U.S. PATENT DOCUMENTS

| 5,753,485 A | 5/1998 | Dwulet et al. |
| 5,830,741 A | 11/1998 | Dwulet et al. |
| 5,989,888 A | 11/1999 | Dwulet et al. |
| 6,458,547 B1 | 10/2002 | Bryan et al. |
| 2004/0053368 A1 | 3/2004 | Ishikawa et al. |
| 2005/0106636 A1 | 5/2005 | Stagljar et al. |
| 2006/0166214 A1 | 7/2006 | Kato et al. |
| 2007/0128596 A1 | 6/2007 | Roninson et al. |
| 2011/0294192 A1 | 12/2011 | Fukushima et al. |
| 2013/0345087 A1 | 12/2013 | Yamagata et al. |

FOREIGN PATENT DOCUMENTS

| CA | 2830140 A1 | 9/2012 |
| CN | 1761749 A | 4/2006 |
| CN | 1977167 A | 6/2007 |
| EP | 1348766 A1 | 10/2003 |
| JP | H09-508026 A | 8/1997 |
| JP | 11504225 A | 4/1999 |
| JP | 2002-159297 A | 6/2002 |
| JP | 2005-521408 A | 7/2005 |
| JP | 2006-145545 A | 6/2006 |
| JP | 2009-077714 A | 4/2009 |
| WO | 96/00283 A1 | 1/1996 |
| WO | 98/24889 A1 | 6/1998 |
| WO | 02/14505 A1 | 2/2002 |
| WO | 2006/006961 A1 | 1/2006 |
| WO | 2010/058707 A1 | 5/2010 |
| WO | 2012/124338 A1 | 9/2012 |

OTHER PUBLICATIONS

Worthington Biochemical Corporation, Clostripain (Endoproteinase-Arg-C) Product Information, Accessed Mar. 20, 2017; Available online at: www.worthington-biochem.com/CP/cat.html.*
Van Deijnen et al., Distribution of collagens type I, type II and type V in the pancreas of rat, dog, pig and man, Cell Tissue Research , vol. 277, Issue 1, (1994), p. 115-121.*
Brandhorst et al., The Ratio Between Class II and Class I Collagenase Determines the Amount of Neutral Protease Activity Required for Efficient Islet Release From the Rat Pancreas, Transplantation Proceedings, 37, (2005), pp. 215-216.*
Serva, Collagenase NB 1, Datasheet, (2008), Available Online at: www.serva.de/www_root/documents/Datasheet_NB1%20GMP%20Grade_1.pdf.*
Inoue, et al., Ultrastructure of Reichert's Membrane, a Multilayered Basement Membrane in the Parietal Wall of the Rat Yolk Sac, The Journal of Cell Biology, vol. 97, 1983, pp. 1524-1537.
Extended European Search Report for EP14745765.9, dated Jun. 29, 2016.
Salamone et al., "Biochemical Comparison Between Clostridium Hystoliticum Collagenases G and H Obtained by DNA Recombinant and Extractive Procedures," Chemical Engineering Transactions, vol. 27, pp. 259-264, Jan. 1, 2012.

(Continued)

*Primary Examiner* — Jennifer M. H. Tichy
(74) *Attorney, Agent, or Firm* — Pearne & Gordon LLP (57) ABSTRACT

Provided is a method for efficiently and stably separating cells having a high biological activity from a biological tissue, by using a degrading-enzyme composition, which is prepared by adding an enzyme for degrading a major protein of the biological tissue in an amount determined depending on the composition of the major protein to a predetermined amount of a neutral protease and/or a protease derived from *Clostridium* sp. According to this method, the type and amount of protein-degrading enzyme to be used for isolating cells can be determined from the composition of a major protein of the biological tissue. Thus, cells having a high biological activity can be efficiently separated while reducing the amount of protein-degrading enzyme to be used.

6 Claims, 6 Drawing Sheets

(56) References Cited

OTHER PUBLICATIONS

Salamone et al., "A New Method to Value Efficiency of Enzyme Blends for Pancreatic Tissue Digestion," Transplantation Proceedings, vol. 42, No. 6, pp. 2043-2048, Jul. 1, 2010.
An Office Action issued in related U.S. Appl. No. 14/003,495 dated Aug. 31, 2015 (total of 16 pages).
Wolters, et al., An analysis of the role of collagenase and protease in the enzymatic dissociation of the rat pancreas for islet isolation; Diabetologia, 1992, vol. 35, pp. 735-742.
Hughes, et al.; "Comparison of the Collagen VI Content Within the Islet-Exocrine Interface of the Head, Body, and Tail Regions of the Human Pancreas"; Transplantation Proceedings; vol. 37; Sep. 2005; pp. 3444-3445.
Hughes, et al.; "Characterisation of Collagen VI within the Islet-Exocrine Interface of the Human Pancreas: Implications for Clinical Islet Isolation?"; Transplantation; vol. 81, No. 3; Feb. 15, 2006; pp. 423-426.
Brandhorst, et al.; "Adjustment of the Ratio Between Collagenase Class II and I Improves Islet Isolation Outcome"; Transplantation Proceedings; vol. 37, Sep. 2005; pp. 3450-3451.
Linetsky, et al.; "Improved Human Islet Isolation Using a New Enzyme Blend, Liberase"; Diabetes; vol. 46; Jul. 1997; pp. 1120-1123.
Watanabe; "Collagenolytic proteases from bacteria"; Applied Microbiology Biotechnol; vol. 63; 2004; pp. 520-526.
Nishi, et al.; "Collagen-binding growth factors: Production and characterization of functional fusion proteins having a collagen-binding domain"; Proc. Natl. Acad. Sci. USA; vol. 95; Jun. 1998; pp. 7018-7023.
Tuan, et al.; "Engineering, Expression and Renaturation of Targeted TGF-Beta Fusion Proteins"; Connective Tissue Research; vol. 34, No. 1; 1996; pp. 1-9.
Han, et al.; "Refolding of a Recombinant Collagen-Targeted TGF-β2 Fusion Protein Expressed in *Escherichia coli*"; Protein Expression and Purification; vol. 11; Jun. 9, 1997; pp. 169-178.
Krahn, et al.; "Fluorescently labeled collagen binding proteins allow specific visualization of collagen in tissues and live cell culture"; Analytical Biochemistry; vol. 350; Jan. 26, 2006; pp. 177-185.
Goto, et al.; "Creation of a system to evaluate the activity exogenous enzymes used in separation of islets of Langerhans"; 37th Meeting of the Japan Society for Pancreas and Islet Transplantation Program and Abstracts; 2010; pp. 1-2.
Brandhorst, et al.; "The Importance of Tryptic-like Activity in Purified Enzyme Blends for Efficient Islet Isolation"; Transplantation; vol. 87, No. 3; Feb. 15, 2009; pp. 370-375.
Meyer, et al.; "Expression pattern of extracellular matrix proteins in the pancreas of various domestic pig breeds, the Goettingen Minipig and the Wild Boar"; Annals of Transplantation; vol. 2, No. 3; pp. 17-26.
Van Suylichem, et al.; "Amount and Distribution of Collagen in Pancreatic Tissue of Different Species in the Perspective of Islet Isolation Procedures"; Cell Transplantation; vol. 4, No. 6; 1995; pp. 609-614.
Carter, et al.; "A Practical Guide to Rodent Islet Isolation and Assessment"; Biological Procedures Online; vol. 11, No. 1; 2009; pp. 3-31.
Yoshida, et al.; "The Influence of Collagen III Expression on the Efficiency of Cell Isolation With the Use of Collagenase H"; Transplantation Proceedings; vol. 46; 2014; pp. 1942-1944.
Fujio, et al.; "Collagenase H is Crucial for Isolation of Rat Pancreatic Islets"; Cell Transplantation; vol. 23; 2014; pp. 1187-1198.

Mccarthy, et al.; "Tissue dissociation enzymes for isolating human islets for transplantation: factors to consider in setting enzyme acceptance criteria"; published in Transplantation; vol. 91, No. 2; Jan. 27, 2011; pp. 137-145, submitted in NIH Public Access publication form, pp. 1-19.
Wolters, et al.; "Different Roles of Class I and Class II Clostridium Histolyticum Collagenase in Rat Pancreatic Islet Isolation"; Diabetes; vol. 44; Feb. 1995; pp. 227-233.
Vos-Scheperkeuter, et al.; "Histochemical Analysis of the Role of Class I and Class II Clostridium Histolyticum Collagenase in the Degradation of Rat Pancreatic Extracellular Matrix for Islet Isolation"; Cell Transplantation; vol. 5, No. 4; 1997; pp. 403-412.
Bauer, et al.; "Structural Comparison of ColH and ColG Collagen-Binding Domains from Colstridium histolyticum"; Journal of Bacteriology; vol. 195, No. 2; Jan. 2013; pp. 318-327.
Knight, et al.; "The Collagen-binding A-domains of Integrins α1β1 and α2β1 Recognize the Same Specific Amino Acid Sequence, GFOGER, in Native (Triple-helical) Collagens"; The Journal of Biological Chemistry; vol. 275, No. 1; Jan. 7, 2000; pp. 35-40, and cover page.
Steffensen, et al.; "Human fibronectin and MMP-2 collagen binding domains compete for collagen binding sites and modify cellular activation of MMP-2"; Matrix Biology; vol. 21; 2002; pp. 399-414.
Rawlings; "A large and accurate collection of peptidase cleavages in the MEROPS database"; Database; vol. 2009; Article ID bap015, doi:10.1093/database/bap015; 2009; pp. 1-14.
Life Technologies; "Probes for Cytoskeletal Proteins"; in The Molecular Probes Handbook: A Guide to Fluorescent Probes and Labeling Technologies; Chapter 11; 11th Edition; 2010; Chapter 11 cover page and p. 477.
International Search Report dated May 22, 2012 for PCT/JP2012/001814.
International Search Report dated Apr. 15, 2014 for PCT/JP2014/000527.
Chinese Office Action dated Dec. 3, 2014 for CN 2012800136123 (7 pages), and corresponding English translation (7 pages).
Office Action dated Jan. 14, 2015 for U.S. Appl. No. 14/003,495; corresponds to 7 pages.
Partial Supplementary European Search Report dated Jan. 30, 2015 for EP 12758377.1; corresponds to 8 pages.
Office Action dated Mar. 27, 2015 for U.S. Appl. No. 14/003,495; corresponds to 9 pages.
Extended European Search Report dated Jun. 8, 2015 for EP 12758377.1; corresponds to 12 pages.
Office Action dated Mar. 28, 2017 for U.S. Appl. No. 14/765,020, 8 pages.
Office Action dated Sep. 19, 2017 for U.S. Appl. No. 14/765,020, 12 pages.
Office Action dated Feb. 23, 2018 for U.S. Appl. No. 14/765,020, 10 pages.
Restriction Requirement dated Jan. 26, 2017 for U.S. Appl. No. 14/765,020, 7 pages.
Clostripain (Endoproteinase-Arg-C) Product Information, Worthington Biochemical Product Catalog, 2 pages.
Japanese Notice of Allowance issued in application No. JP2014-559602 dated Nov. 27, 2018; 3 pages.
Mallya et al., "Kinetics of Hydrolysis of Type I, II, and III Collagens by the Class I and II Clostridium histolyticum Collagenases," Journal of Protein Chemistry, vol. 11, No. 1, pp. 99-107(1992).
Matsushita et al., "Gene Duplication and Multiplicity of Collagenases in Clostridium histolyticum," Journal of Bacteriology, vol. 181, No. 3, pp. 923-933 (1999).
Office Action for corresponding Japanese Application No. JP 2018-148176 dated Jul. 16, 2019.

* cited by examiner

METHOD FOR SEPARATING CELL FROM BIOLOGICAL TISSUE

CROSS-REFERENCE TO RELATED APPLICATIONS

This application is a continuation of U.S. application Ser. No. 14/765,020, filed Jul. 31, 2015, which is a national stage application of International Appl. PCT/JP2014/000527, filed Jan. 31, 2014, and which claims priority of Japanese Patent Appl. No. 2013-018774, filed Feb. 1, 2013, all of which are hereby incorporated by reference.

TECHNICAL FIELD

The present invention relates to a method for separating cells from a biological tissue, and particularly to a method for efficiently and stably separating cells having a high biological activity by controlling the amount of protein-degrading enzyme to be used.

BACKGROUND ART

Enzymatic isolation of cells or cell aggregates (cell clusters), which are present in various organs and tissues such as liver, pancreas, kidney, periodontal tissue, skin, cartilage, bone and nervous tissue of multicellular animals such as mammals, birds, reptiles and fish as well as in an ES cell tissue and a fibroblast cell tissue serving as a material for inducible pluripotent stem cells (iPS cells), is useful in a wide variety of usages including cell transplantation, cell strain establishment, therapy, diagnosis, and examination. For example, diabetes is treated by a medical procedure in which pancreatic islets are isolated from a pancreas and transplanted to a patient. For pancreatic islet transplantation, it is essential to separate a cell aggregate called as pancreatic islets present in the pancreas tissue. At this time, it is necessary to separate pancreatic islets by degrading the pancreas tissue without damaging the pancreatic islets. Furthermore, liver failure and the like are treated by separating liver cells from a liver and transplanting them into a patient.

In order to dissociate a biological tissue and separate cells or cell aggregates contained in the biological tissue, it is necessary to separate cells or the like to a desired level and separate the cells from the other portion of the biological tissue. In separating cells or the like from a biological tissue by enzymatic isolation, it is necessary to treat intercellular matrix with a protein-degrading enzyme such as collagenase.

A biological tissue is constituted of cells and intercellular matrix (intercellular substance). The intercellular substance is a substance anchoring cells and includes a structural material and a non-structural material. Examples of the structural material include fibers such as a collagen fiber, an elastic fiber and a fine retinal fiber. Examples of the non-structural material, which is a component filling the space between fibers, called as a substrate and refers to sol or gel substance, include a sugar protein and a proteoglycan.

A typical intercellular substance is a protein called collagen which represents about ⅓ of in-vivo total protein weight. Collagen has a fiber structure and is officially called as a collagen fiber or a collagenous fiber.

The tissues are roughly classified into four categories: an epithelial tissue, a supporting tissue, a muscular tissue and a nervous tissue. The epithelial tissue is a tissue covering the surface of a body or organs and consisting of highly dense cells without the intercellular substance interposed therebetween. The supporting tissue, which plays a role in supporting e.g., a body, organs and cells, includes a connective tissue, a cartilaginous tissue, a bone tissue, blood and lymph. The muscular tissue is integrally formed of cells differentiated for the purpose of contraction motion, in which the ratio occupied by the intercellular substance is extremely low. The muscular tissue is constituted of muscle cells, a connective tissue, blood vessels and nerves; however, a major structure thereof is a muscle fiber. The nervous tissue is primarily constituted of the endoneurium and the perineurium, each containing a large amount of intercellular substance (collagen).

The connective tissue, which is a kind of supporting tissue, refers to an adipose tissue and a fibrous connective tissue. As the structural components of the fibrous connective tissue, a collagen fiber and an elastic fiber are mentioned. The fibrous connective tissues are roughly divided into a hydrophobic connective tissue and a dense connective tissue. The hydrophobic connective tissue refers to a fibrous connective tissue having collagen fibers irregularly arranged therein and distributed in e.g., a subcutaneous tissue, a mucous membrane tissue, nerve, adventitia, and an interlobular tissue.

A peptide chain of collagen characteristically have a primary structure in which glycine repeatedly appears every third residue, like "-glycine-amino acid X-amino acid Y". It is known that there are about 30 types of molecule species in human collagen. The collagen most abundantly present in a body is fibrous I-type collagen. Non-fibrous collagen IV is also abundantly contained. Collagen IV fibers are linked with each other via an intermolecular disulfide bond and participated in formation of a reticular tissue (Non Patent Literature 1). It has been reported that collagen VI is present between the pancreatic islets and the endocrine tissue (Non Patent Literatures 2 and 3).

As to the enzymes for degrading tissue, various types of crude collagenases derived from *Clostridium histolyticum* contain not only collagenase but also various proteases (having collagen degradation activity and nonspecific protein degradation activity) and non-protease components (e.g., phospholipase). By virtue of the crude collagenase, cells and cell populations are enzymatically separated from almost all biological tissues.

It is known that a pancreatic islet tissue is also degraded by a protein-degrading enzyme selected from the group consisting of two types of collagenases (Col G and Col H) derived from *Clostridium histolyticum*, a protease (thermolysin, Dispase or neutral protease (NP) derived from *Clostridium histolyticum*) (Patent Literatures 1 and 2). For example, two types of collagenases and a neutral metallo protease produced by *Clostridium histolyticum* are known to be preferably used (Non Patent Literature 4). In enzymatically separating cells or the like from a biological tissue, two types of collagenases are reported to have important roles in attaining the yield and keeping biological activity of the cells or the like to be separated (Non Patent Literature 5).

It is also reported that the number of pancreatic islets separated from a human pancreas increases in proportion to an α-N-benzoyl-L-arginine ethyl ester hydrochloride (BAEE) degradation activity that an enzyme mixture exhibits (Patent Literature 1 and Non Patent Literature 6). As the enzyme having a BAEE degradation activity, clostripain (CP) produced by *Clostridium histolyticum* is known.

The state of intercellular matrix in a biological tissue (particularly, collagen content) varies depending upon the organism species, age, sex, tissue, living environment and etc. How much collagen is contained in which state of matrix of which tissue has not yet been elucidated. Collagen is present in a wide variety of species from mammals to fish and difference in constituent collagen between species has not yet been elucidated.

It seems to be possible that whether or not a specific type of collagen is present in the matrix of a biological tissue is determined by immuno-staining using antibodies against individual types of collagens. However, since many types of collagens are present and collagens are present in a wide variety of multicellular animals, it is difficult to produce antibodies. Because of these problems, it is difficult to realize identification of the specific type of collagen.

CITATION LIST

Patent Literature

Patent Literature 1: International Publication No. 1996/00283
Patent Literature 2: International Publication No. 1998/24889

Non Patent Literature

Non Patent Literature 1: Inoue et al., J Cell Biol, 97, 1524-1539 (1983)
Non Patent Literature 2: S J Hughes, P McShane, Transplant Proceedings, 37, 3444-34445 (2005)
Non Patent Literature 3: S J Hughes, A Clark, P McShane, Transplantation, 81(3) 423-426 (2006)
Non Patent Literature 4: E Linetsky et al., Diabetes, 46, 1120-1123 (1997)
Non Patent Literature 5: D Brandhorst et al., Transplantation Proceedings, 37(8), 3450-3451 (2005)
Non Patent Literature 6: H Brandhorst et al., Transplantation, 87(3), 370-375 (2009)

SUMMARY OF INVENTION

Technical Problem

In separating cells or cell aggregates from a biological tissue, it is not easy to degrade only various structural proteins constituting intercellular matrix of the biological tissue and organs with a protein-degrading enzyme without degrading and damaging the surface of target cells or the like to be separated. As described above, the state (particularly, collagen content) of intercellular matrix in a biological tissue varies depending upon the organism species, age, sex, tissue, living environment, etc. Particularly, collagen significantly changes in physical properties depending upon aging.

It is known that a human organ acts differently in response to a protein-degrading enzyme depending upon e.g., the age, sex, habit and medical history; however, a means for determining the type and amount of optimal protein-degrading enzyme has not so far been developed. In the present situation, isolation had to be performed by empirically determining the type of enzyme and reaction time thereof. Pancreatic islets are separated in accordance with a protocol, more specifically, a medical worker treats a pancreas with a predetermined amount of enzyme only by varying the time of degradation while visually checking the degree of degradation of the pancreas. For this reason, the quantity and quality of the pancreatic islets to be obtained inevitably varies depending upon the state of a target pancreas.

In view of the above circumstance, a main object of the present invention is to provide a cell separation method by which cells having a high biological activity can be efficiently and stably separated from a biological tissue.

Solution to Problem

In order to solve the aforementioned problems, the present invention provides the following methods.

[1] A method for separating cells from a biological tissue, using a degrading-enzyme composition, which is prepared by adding an enzyme for degrading a major protein of the biological tissue in an amount determined depending on the composition of the major protein to a predetermined amount of a neutral protease and/or a protease derived from *Clostridium* sp.

[2] The method according to [1], including a step of determining the composition of the major protein of the biological tissue; a step of preparing a degrading-enzyme composition by adding an enzyme for degrading the major protein in an amount determined depending on the composition determined to the predetermined amount of a neutral protease and/or a protease derived from *Clostridium* sp.; and a step of treating the biological tissue with the degrading-enzyme composition prepared.

According to this method, the type and amount of protein-degrading enzyme to be used for isolating cells can be determined based on the composition of the major protein of a biological tissue. Thus, cells having a high biological activity can be efficiently separated by controlling the amount of protein-degrading enzyme to be used.

[3] The method according to [1] or [2], in which the enzyme for degrading the major protein is collagenase H and/or collagenase G of *Clostridium* sp.

[4] The method according to any of [1] to [3], in which the major protein is collagen I and/or collagen III.

[5] The method according to [4], in which the amount ratio of collagenase H and/or collagenase G to be added to the degrading-enzyme composition is determined in accordance with the composition of collagen I and/or collagen III.

[6] The method according to any of [1] to [5], in which the neutral protease is thermolysin or a neutral protease derived from *Clostridium* sp.

[7] The method according to any of [1] to [6], in which the protease derived from *Clostridium* sp. is a protease having an α-N-benzoyl-L-arginine ethyl ester hydrochloride (BAEE) degradation activity.

[8] The method according to any of [1] to [7], in which the protein composition of the biological tissue is determined by an enzymatic immunoassay.

[9] A method for separating pancreatic islets from a pancreas tissue, using a degrading-enzyme composition, which is prepared by adding collagenase H and/or collagenase G derived from *Clostridium* sp. in an amount sufficient to degrade collagen I and/or collagen III and in accordance with a composition of collagen I and/or collagen III of the pancreas tissue, to a predetermined amount of a neutral protease and/or a protease derived from *Clostridium* sp.

[10] The method according to [9], in which the weight ratio (H/G) of collagenase H and collagenase G in the degrading-enzyme composition is 0.35 or more.

[11] The method according to [9] or [10], in which the degrading-enzyme composition contains a neutral protease derived from *Clostridium* sp. as the neutral protease, and a protease having an α-N-benzoyl-L-arginine ethyl ester hydrochloride (BAEE) degradation activity as the protease derived from the *Clostridium* sp.

[12] A method for separating liver cells from a liver tissue, using a degrading-enzyme composition, which is prepared by adding collagenase H and/or collagenase G of *Clostridium* sp. in an amount sufficient to degrade collagen I and/or collagen III and in accordance with a composition of collagen I and/or collagen III of the liver tissue, to a predetermined amount of a neutral protease and/or a protease derived from *Clostridium* sp.

[13] The method according to [11], in which the weight ratio (H/G) of collagenase H and collagenase G in the degrading-enzyme composition is 0.25 or less.

[14] A method for separating pancreatic islets from a pancreas tissue, using a degrading-enzyme composition containing a neutral protease derived from *Clostridium* sp. and a protease having an α-N-benzoyl-L-arginine ethyl ester hydrochloride (BAEE) degradation activity.

[15] The method according to [14], in which the protease having the BAEE degradation activity is clostripain.

In the present invention, the "biological tissue" includes, but not particularly limited to, various organs and tissues of multicellular animals such as mammals, birds, reptiles and fish. Examples thereof may include liver, pancreas, kidney, periodontal tissue, skin, cartilage, bone and nervous tissue. Furthermore, an ES cell tissue and a fibroblast cell tissue serving as a material for an inducible pluripotent stem cells (iPS cells) are included in the "biological tissue".

The "cells" include cells and cell aggregates and all types of cells present in the above biological tissues may be included. Examples of the "cells" may include hepatocytes, pancreatic islets and glomeruli.

Advantageous Effects of Invention

Owing to the present invention, a method for efficiently and stably separating cells having a high biological activity from a biological tissue is provided.

DESCRIPTION OF EMBODIMENTS

Now, a preferred embodiment for carrying out the present invention will be described below. Note that the embodiment described below is a typical embodiment of the present invention and should not be construed as limiting the scope of the present invention.

The present inventors found that, of various collagen degrading enzymes, collagenase H (ColH) is a very important enzyme in degrading a biological tissue (see Reference Example 1 described later). Since it has been considered in the art that collagenase G (ColG) is more important in degrading a biological tissue (see Patent Literatures and Non Patent Literatures in the above), the finding is a matter of surprise. The present inventors have also found that Col H degrades collagen I and collagen III, which are major proteins in a biological tissue (see Reference Example 2 described later).

The present inventors have also revealed that if the abundance of collagen I and collagen III, which are major proteins that Col H degrades, in a biological tissue is measured, the amount of protein-degrading enzyme suitably used for separating cells from the biological tissue can be previously determined, with the results that the cells can be separated without excessively being damaged (see Example 1). The present inventors have further found that a neutral protease (NP) of *Clostridium* sp. serving as a neutral protease and a protease having a BAEE degradation activity synergistically work to enhance the efficiency of separating pancreatic islets from a pancreas tissue (see Example 2).

In this way, a method for separating cells from a biological tissue using a degrading-enzyme composition, which is prepared by adding a major protein-degrading enzyme of the biological tissue in an amount determined depending on the composition of the major protein, was conceived. According to the method for separating cells, it is possible to determine the type and amount of protein-degrading enzyme to be used for isolating cells based on the composition of the major protein of the biological tissue. Thus, cells having a high biological activity can be efficiently separated while reducing the amount of protein-degrading enzyme to be used.

[Major Protein]

In the method for separating cells according to the present invention, the major protein is a protein constituting intercellular matrix and may possibly vary depending upon the target biological tissue. Examples of collagen include collagen I, collagen II, collagen III, collagen IV, collagen V, laminin, fibronectin and vitronectin. For example, when cells are separated from a pancreas tissue and a liver tissue, the major protein preferably includes collagen I and collagen III.

[Composition of Major Protein]

In the method for separating cells according to the present invention, the composition of the major protein refers to the ratio of the major protein in the proteins constituting intercellular matrix or the amount thereof. For example, when cells are separated from a pancreas tissue and a liver tissue, the composition of major protein refers to the ratios or amounts of collagen I, collagen II, collagen III, collagen IV, collagen V, collagen VI, laminin, fibronectin and vitronectin; and particularly refers to the ratios or amounts of collagen I and collagen III.

The composition of the major protein can be determined by enzymatic immunoassay using a specific antibody against the major protein and a specific inhibitory peptide thereof. More specifically, a labeled antibody or inhibitory peptide is allowed to react with a biological tissue slice, for example, by an immunohistological approach. Next, the intensity of a signal from the label attached to the antibody or inhibitory peptide bound to the major protein is visually checked under observation of a microscope or detected by an apparatus. In this manner, the major protein is quantified and the composition is determined. The composition of the major protein can be also determined quickly by e.g., a sedimentation reaction in gel, immunoelectrophoresis, an immunoturbidimetric method or an enzyme immunoassay using an antibody.

[Major Protein-Degrading Enzyme]

In the method for separating cells according to the present invention, a major protein-degrading enzyme may possibly vary depending upon the target biological tissue. For example, when cells are separated from a pancreas tissue and a liver tissue, the degrading enzymes for a major protein are Col H and Col G. When pancreatic islets are separated from a pancreatic islet tissue, Col H is important as a major protein-degrading enzyme; whereas when liver cells are separated from a liver tissue, Col G is important as a major protein-degrading enzyme.

[Degrading-Enzyme Composition]

The degrading-enzyme composition to be used is preferably prepared by adding the aforementioned major protein-degrading enzyme to a predetermined amount of a neutral protease and/or a protease derived from *Clostridium* sp.

As the neutral protease, for example, thermolysin or a neutral protease (NP) derived from *Clostridium* sp. is mentioned.

As the protease derived from *Clostridium* sp., a protease having an α-N-benzoyl-L-arginine ethyl ester hydrochloride (BAEE) degradation activity is mentioned. The protease having a BAEE degradation activity is preferably clostripain (CP). Since *Clostridium* sp. strain produces various types of proteases, an enzyme produced as a recombinant protein is desirably used as the protease derived from *Clostridium* sp. strain.

The degrading-enzyme composition to be used for separating pancreatic islets from a pancreas tissue preferably contains both a neutral protease (NP) derived from *Clostridium* sp. as a neutral protease and a protease having a BAEE degradation activity as the protease derived from *Clostridium* sp. NP and the protease having a BAEE degradation activity synergistically work to exert an effect of increasing the number of pancreatic islets to be separated from a pancreas tissue.

The amount of a neutral protease and/or a protease derived from *Clostridium* sp. in a degrading-enzyme composition, which is not particularly limited, is, for example, 0.3 to 0.5 mg per composition (10 mL). Note that the content of the enzyme in a degrading-enzyme composition may appropriately be controlled also in accordance with the weight of the target biological tissue to be treated.

The amount of major protein-degrading enzyme added to a degrading-enzyme composition is determined based on the composition of the aforementioned major protein. More specifically, the amount of major protein-degrading enzyme is determined based on the ratio or amount of major protein in the proteins constituting intercellular matrix. More specifically, for example, if the proteins constituting the intercellular matrix are Collagen III and collagen I, the amounts of Col H and Col H to be used are determined based on the ratios or amounts of collagen III and collagen I. Particularly favorably, the amount ratios of Col H and Col G to be used in the degrading-enzyme composition are determined based on the ratios or amounts of collagen III and collagen I.

For example, when pancreatic islets are separated from a pancreas tissue in which the ratios of collagen III and collagen I in the proteins constituting intercellular matrix are high (amounts are large), the amount of Col H to be used is preferably 0.35 times or more as large as that of collagenase G. Note that pancreatic islets can be separated by using a degrading-enzyme composition containing only collagenase H (of collagenase G and collagenase H) although separation efficiency decreases. In contrast, when liver cells are separated from a liver tissue in which the contents of collagen III and collagen I are small, the amount of Col H to be used is preferably 0.25 times or less as small as that of collagenase G.

For example, when pancreatic islets are separated from a pancreas tissue, a degrading-enzyme composition can be prepared by adding, to thermolysin (0.3 mg), high purity Col G (2 mg) and Col H (1.1 mg) (0.55 times as large as collagenase G) produced by recombination per composition (10 mL). Furthermore, when liver cells are separated from a liver tissue, a degrading-enzyme composition can be prepared by adding, to thermolysin (0.5 mg), high purity Col G (14.4 mg) and Col H (3.6 mg) (0.25 times as large as collagenase G) per composition (10 mL).

[Enzyme Treatment]

A biological tissue may be treated with a degrading-enzyme composition in the same manner as in a conventional method. The degrading-enzyme composition contains a major protein-degrading enzyme in an amount (the minimum requisite amount) required for degradation of the biological tissue based on the composition of the major protein of the biological tissue. Thus, desired cells can be separated from a biological tissue without producing a problem such as a reduction of physiological activity of separated cells and a reduction of yield caused by an excessive or insufficient content of enzyme in a degrading-enzyme composition.

As described above, according to the method for separating cells according to the present invention, cells having a high biological activity can be efficiently and stably separated from a biological tissue by determining the composition of the major protein in a biological tissue and preparing a degrading-enzyme composition by adding the enzyme for degrading the major protein in a requisite amount. In short, according to this method, high quality cells can be separated in a high yield by applying an optimal enzymatic treatment to any target biological tissue.

EXAMPLES

Reference Example 1: Identification of Major Protein-Degrading Enzyme to be Used in Separating Cells or the Like from Biological Tissue

[Identification of Enzyme for Use in Separating Pancreatic Islets from Rat's Pancreas Tissue]

A male Lewis rat (10 to 13 weeks old) was used. Before the pancreas was excised out, the duodenum was clamped. A degrading-enzyme composition (10 mL, cold Hank's Balanced Salt Solution (HBSS)), which contains at least one of a protein-degrading enzyme: recombinant collagenase G (8.4 mg) and collagenase H (2.9 mg), and a neutral protease: thermolysin (0.3 mg), was injected through the bile duct. After a treatment was performed at 37° C. for 14 minutes, density gradient centrifugation was performed to obtain a fraction of pancreatic islets.

The case (GH group) where thermolysin, collagenase G and collagenase H were simultaneously added, the case (G group) where thermolysin and collagenase G alone were added, and the case (H group) where thermolysin and collagenase H alone were added, were evaluated for yield and a biological activity of pancreatic islets. The results are shown in FIGS. 1 to 5. In the SGS test (FIG. 5), the volume ratio of insulin secreted at the time of exposure to high concentration glucose (16.7 mM) and insulin secreted at the time of exposure to low concentration glucose (1.67 mM) was obtained and used as a stimulation index for evaluation.

Figure 1:
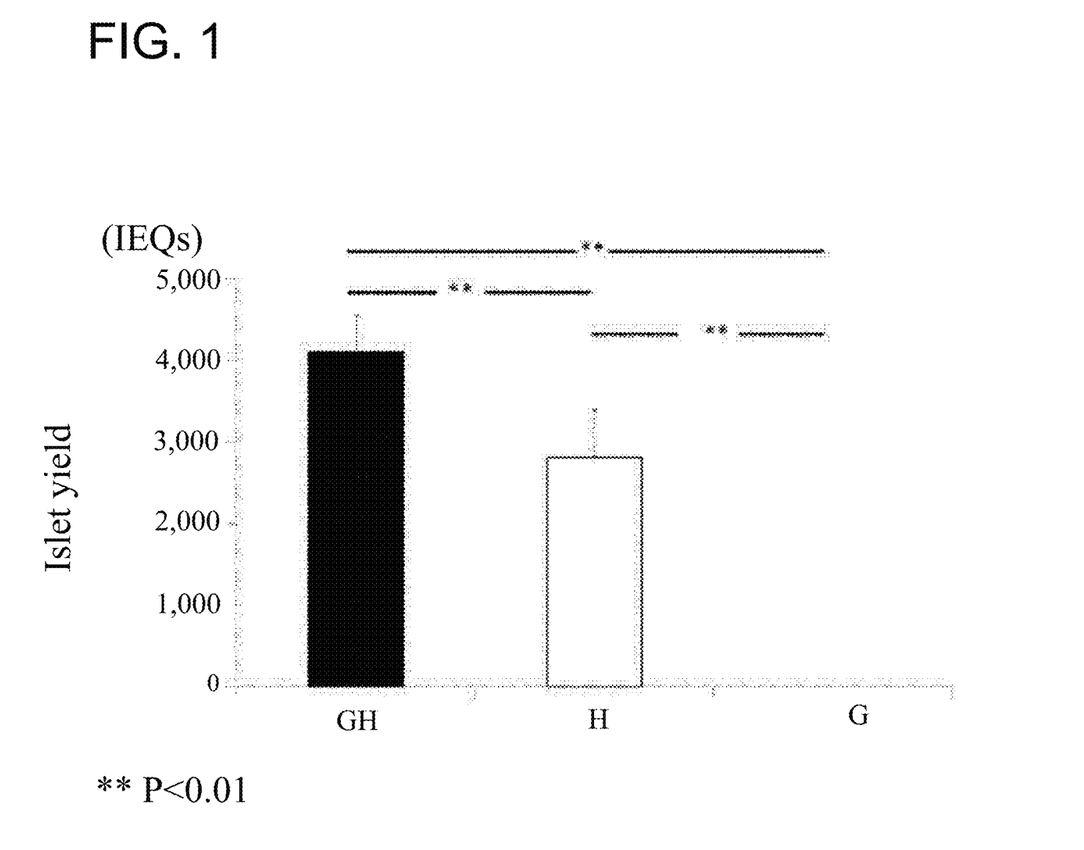
FIG. 1 is a graph showing the yield of pancreatic islets (Reference Example 1).
Figure 2:
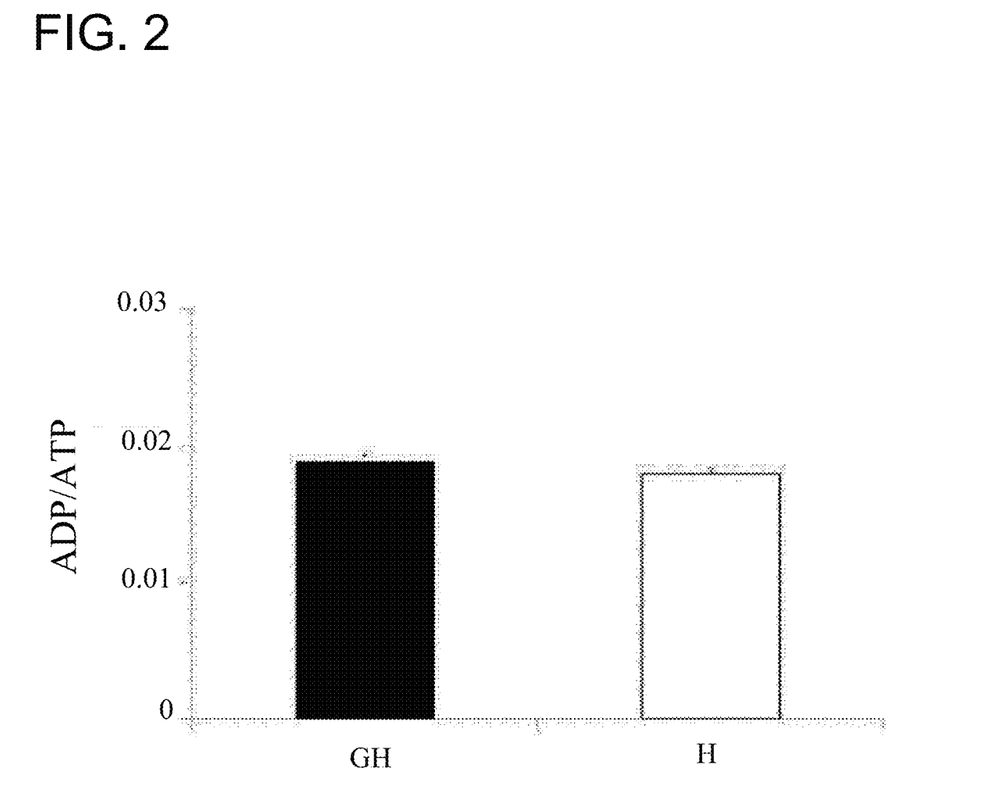
FIG. 2 is a graph showing measurement results of the ADP/ATP value of the pancreatic islets separated (Reference Example 1).
Figure 3:
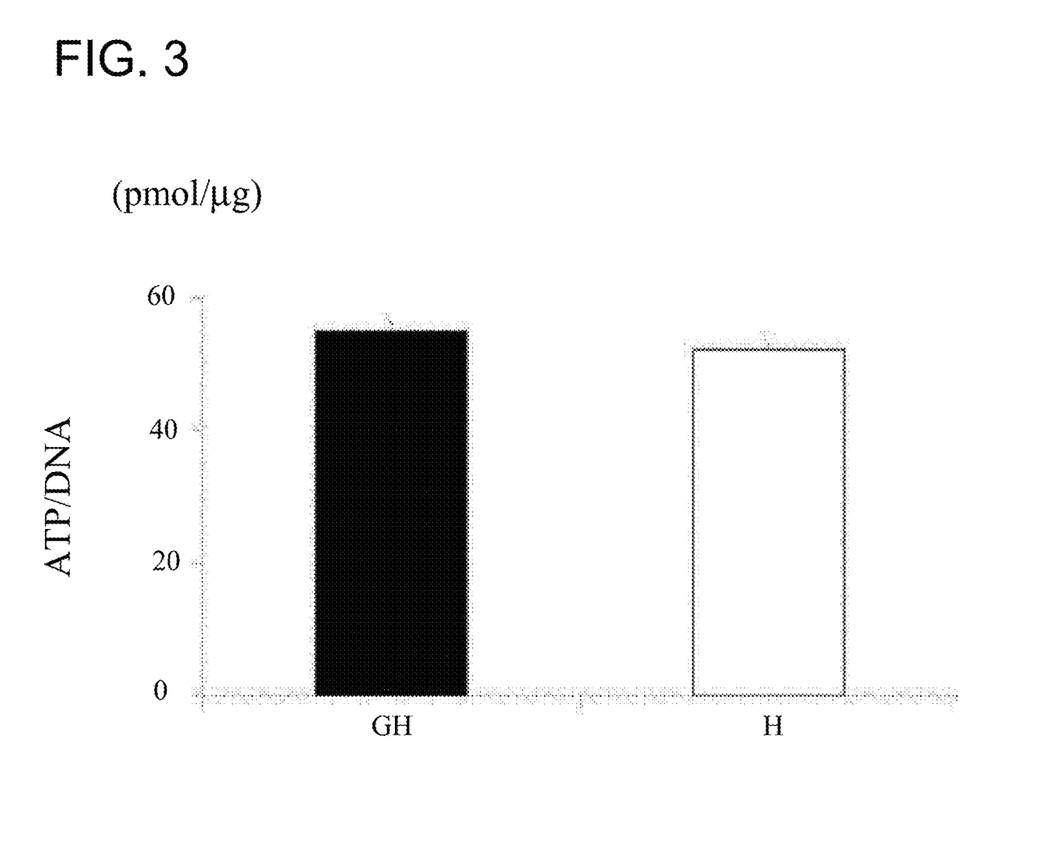
FIG. 3 is a graph showing measurement results of the ATP/DNA value of the pancreatic islets separated (Reference Example 1).
Figure 4:
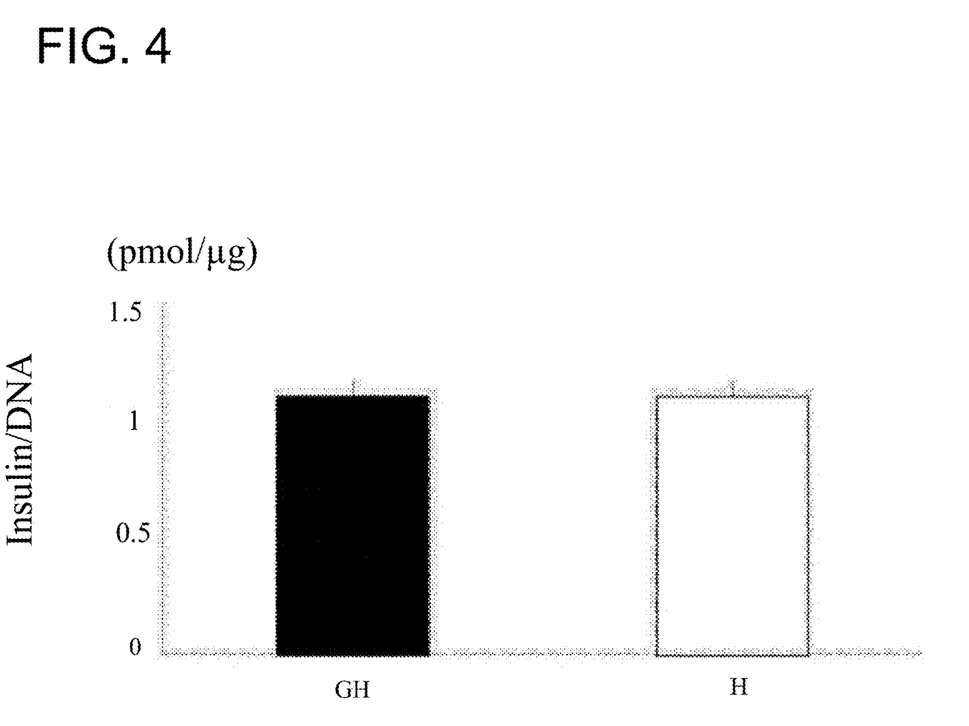
FIG. 4 is a graph showing measurement results of the Insulin/DNA value of the pancreatic islets separated (Reference Example 1).
Figure 5:
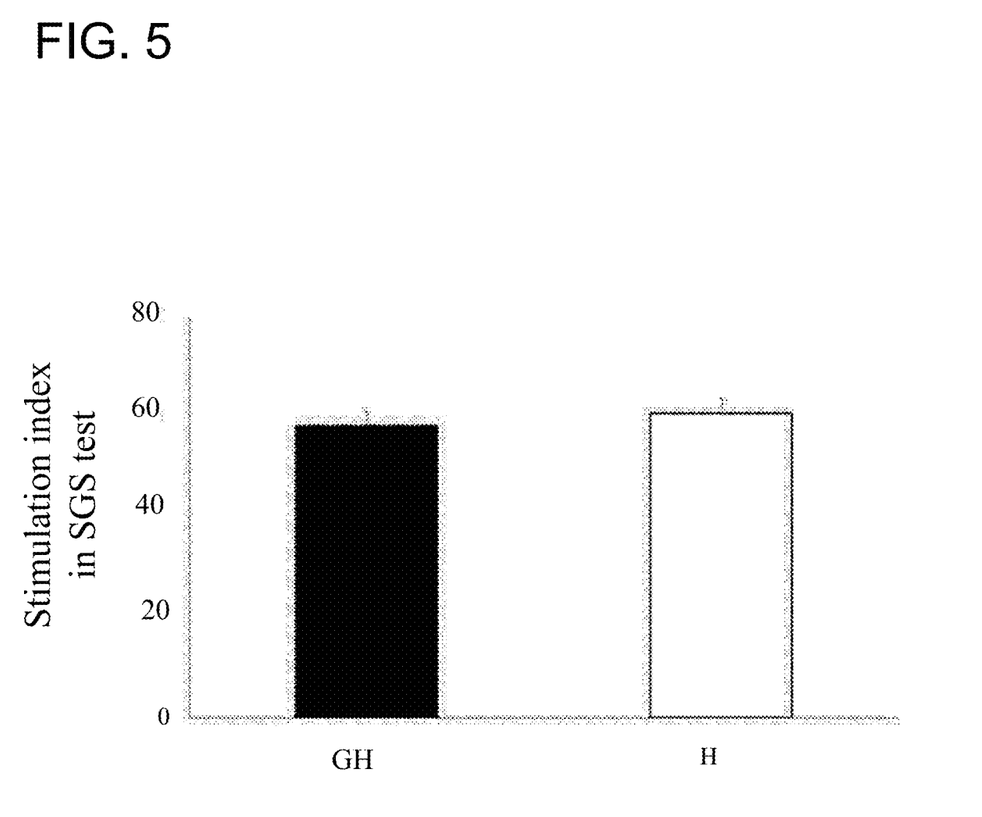
FIG. 5 is a graph showing evaluation results of the stimulation index of the separated pancreatic islets in SGS test (Reference Example 1).

As shown in FIG. 1, pancreatic islet yield (islet equivalents (IEQs)) of the H group was 70% of that of the GH group. In contrast, in the G group, none of pancreatic islets were separated. As is apparent from the ADP/ATP value of pancreatic islets (FIG. 2), ATP/DNA value thereof (FIG. 3), insulin/DNA value thereof (FIG. 4) and stimulation index (FIG. 5) in the SGS test, the pancreatic islets obtained in the H group had the same physiological activity as those of the pancreatic islets obtained in the GH group. From these results, collagenase H was identified as the major protein-degrading enzyme to be used in separating pancreatic islets from a pancreas tissue.

[Identification of Enzyme for Use in Separating Liver Cells from Rat's Liver Tissue]

A degrading-enzyme composition (10 mL, HBSS), which contains at least one of a protein-degrading enzyme: recombinant collagenase G (14.4 mg), collagenase H (3.6 mg), and a neutral protease: thermolysin (0.5 mg), was prepared. The liver tissue (10 to 12 g) was treated with the degrading-enzyme composition prepared at 37° C. for 7 minutes and then subjected to density gradient centrifugation to separate liver cells.

In the case (GH group) where a degrading-enzyme composition prepared by blending collagenase G and collagenase H with thermolysin was used, $5.02±2.11×10^8$ of liver cells were successfully separated. In the case (G group) where a degrading-enzyme composition prepared by adding collagenase G to thermolysin was used, $0.81±0.11×10^6$ of liver cells were successfully separated. In contrast, in the case (H group) where a degrading-enzyme composition prepared by adding collagenase H to thermolysin was used, the liver cells could not be separated. From these results, collagenase G was identified as the major protein-degrading enzyme to be used in separating liver cells from a liver tissue.

Reference Example 2: Identification of Substrate for Major Protein-Degrading Enzyme

[Identification of Substrate for Collagenase H]

The pancreas tissue slices (100 mg) of a Lewis rat were treated with 20 mM HEPES (pH8.0) containing a protease inhibitor cocktail (Roche) and 1 mM $CaCl_2$ at 37° C. overnight. Thereafter, the tissue slices were washed with a buffer and subjected to enzyme degradation with a buffer containing collagenase H (0.1 mg/mL) for 10 hours at 37° C.

After the enzyme degradation, incubation was performed in 50% acetonitrile containing 100 mM TMPP (Sigma-Aldrich) (10 μL) for 30 minutes. Then, acetone precipitation was performed with cold acetone and thereafter centrifugation was performed. The resultant precipitate was dried and digested with trypsin (10 μL/mg) in a 100 mM ammonium carbonate solution, overnight.

After the digest was treated by ZipTip (Millipore), the resultant peptides were eluted by concentration gradient with 2.5-40% acetonitrile in 10% formic acid and subjected to mass analysis by an LTQ Orbitrap XL mass spectrometer (Terumo Fisher Scientific Inc). Database was searched by using MASCOT Software 1 program.

Figure 6:
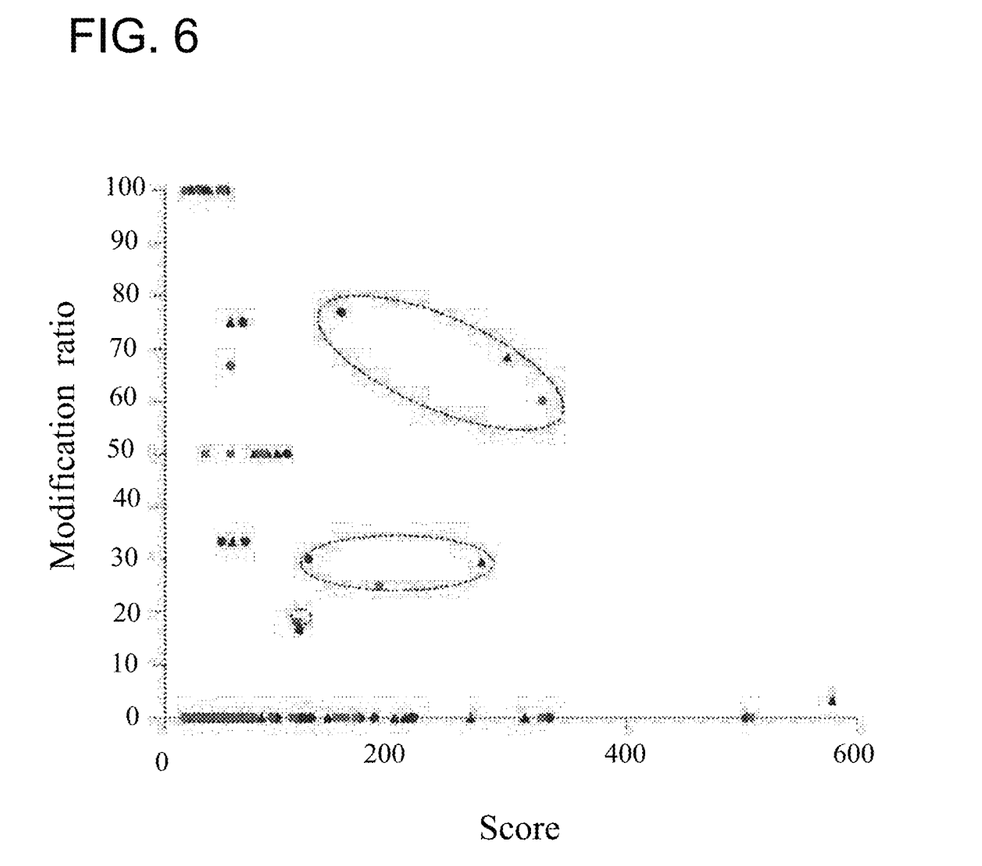
FIG. 6 is a graph showing measurement results of the amount of TMPP attached to collagen I and collagen III degraded by collagenase H (Reference Example 2).

Using the TMPP label attached to the N-terminal of the cleaved protein (fragment) as an index, which protein is degraded by collagenase H can be identified. FIG. 6 shows the TMPP modification ratio of collagen I and collagen III fragments cleaved with collagenase H. In the figure, data regarding collagen III were plotted within the upper dotted line circle; whereas data regarding collagen I were plotted within the lower dotted line circle.

It was revealed that 70% of collagen III and 20% of collagen I are degraded by collagenase H. By this, it was demonstrated that major proteins, i.e., substrates for collagenase H, are collagen III and collagen I.

Example 1: Separation of Cells Depending Upon the Composition of Major Protein of Biological Tissue

[Quantification of Collagen III and Collagen I in Pancreas Tissue and Liver Tissue of Rat]

Tissue slices of a Lewis rat (10 to 13 weeks old) were prepared. Enzymatic immunoassay using labeled antibodies (Chemicon Merck Millipore) against collagen III and collagen I was performed to compare expression of collagen III and collagen I in the pancreas tissue and liver tissue. As a result, the number of positive staining obtained by immunohistostaining of collagen III and collagen I in the liver tissue was significantly lower than that in the pancreas tissue.

[Separation of Cells from Pancreas Tissue and Liver Tissue of Rat]

It was predicted that the major protein of a liver tissue may be a protein other than collagen III and collagen I, and thus the amount of collagenase H in the degrading-enzyme composition for liver cell separation may be low compared to for pancreatic islet separation.

A liver tissue (10 to 12 g) was treated with a degrading-enzyme composition (10 mL HBSS) containing protein-degrading enzymes: thermolysin (0.5 mg), recombinant collagenase G (14.4 mg) and collagenase H (3.6 mg, which is 0.25 times as large as collagenase G) at 37° C. for 7 minutes and then subjected to density gradient centrifugation. Liver cells ($5.02±2.11×10^8$) were favorably separated.

A degrading-enzyme composition (10 mL HBSS) containing protein-degrading enzymes: thermolysin (0.3 mg), recombinant collagenase G (8.4 mg) and collagenase H (2.9 mg, which is 0.35 times as large as collagenase G) was injected through the bile duct and treatment was performed at 37° C. for 14 minutes, and then, density gradient centrifugation was performed. Pancreatic islets (about 4000 islets) were favorably separated.

It was found that, in the separation of pancreatic islets from a pancreas tissue where the ratios of collagen III and collagen I in proteins constituting the intercellular matrix are high (the amounts are large), a degrading-enzyme composition containing a larger amount of collagenase H (0.35 times as large as collagenase G) is preferably used; in contrast, in the separation of liver cells from a liver tissue where the contents of collagen III and collagen I are small, a degrading-enzyme composition containing a relatively small amount of collagenase H (0.25 times as large as collagenase G) is preferably used. By previously measuring the ratios or amounts of major proteins (collagen III and collagen I) in proteins constituting the intercellular matrix of a tissue, the amount of protein-degrading enzyme suitably used for separating cells from the tissue, more specifically, the amount ratio of collagenase H and collagenase G to be used was successfully determined.

Example 2: Synergetic Effect of NP and CP in Separating Pancreatic Islets from Pancreatic Islet Tissue A degrading-enzyme composition containing, in addition to collagenase G (8.4 mg) and collagenase H (2.9 mg), any one or two of thermolysin, neutral protease (NP) derived from *Clostridium* sp. and clostripain (CP) in various amounts to be added, was prepared. Pancreatic islets were separated from the pancreatic islet tissue by using the degrading-enzyme composition prepared in the same manner as in Reference Example 1 and the numbers of pancreatic islets were compared.

NP and CP were obtained by introducing an NP gene or a CP gene derived from *Clostridium histolyticum* into *Bacillus subtilis* and expressing them followed by performing purification and then put in use.

In the case where a degrading-enzyme composition containing NP was used and the case where a degrading-enzyme composition containing thermolysin and CP was used, the number of separated pancreatic islets decreased compared to the case where a degrading-enzyme composition containing thermolysin was used. In contrast, in the case where a degrading-enzyme composition containing NP and CP was used, the number of separated pancreatic islets significantly increased compared to the case where a degrading-enzyme composition containing thermolysin was used. In addition, in the case where a degrading-enzyme composition containing NP and CP was used, the number of separated pancreatic islets was found to increase depending upon the amounts of NP and CP used.

From these results, it was revealed that neutral protease (NP) derived from *Clostridium* sp. and protease (CP) having a BAEE degradation activity synergistically work to exert an effect of increasing the number of pancreatic islets to be separated from a pancreatic islet tissue.

INDUSTRIAL APPLICABILITY

According to the method for separating cells of the present invention, cells having a high biological activity can be efficiently and stably separated from a biological tissue. Accordingly, the method for separating cells is useful in a wide variety of usages such as cell transplantation, cell strain establishment, therapy, diagnosis and examination of a disease caused by specific cells.

Furthermore, if specific substrates for individual enzyme components present on a tissue are identified and prepared in the form of a kit, cell separation can be optimized for individual donor tissue in a tailor made manner. In separation of pancreatic islets so far made in the art, a tool having a prefixed composition must be applied to various pancreatic tissues of donors totally different in matrix composition. However, if highly pure, safe and stable enzyme components are prepared by introduction of biotechnology and specific substrates for the enzyme components present on a pancreatic tissue are identified and prepared in the form of a kit, pancreatic islets that can be adapted to a donor's pancreas can be separated in a tailor made manner.

The invention claimed is:

1. A method for separating pancreatic islets from a pancreas tissue, using a degrading-enzyme composition, comprising:
    measuring an abundance of collagen I and collagen III in the pancreas tissue,
    determining an amount ratio of collagenase H to collagenase G derived from *Clostridium* sp. based on the measured abundance of collagen I and collagen III, wherein a higher amount ratio is used when the measured abundance is higher and a lower amount ratio is used when the measured abundance is lower,
    preparing the degrading-enzyme composition by adding collagenase H and collagenase G derived from *Clostridium* sp. with the determined ratio, to a predetermined amount of one or more of a neutral protease or a protease derived from *Clostridium* sp.,
    treating the pancreas tissue with the degrading-enzyme composition, and
    separating pancreatic islets from the pancreas tissue treated with the degrading-enzyme composition,
    wherein collagenase H degrades collagen I and collagen III, and
    wherein the amount ratio (H/G) of collagenase H to collagenase G in the degrading-enzyme composition is 0.35 or more.

2. The method according to claim 1, wherein the abundance of collagen I and collagen III in the pancreas tissue is measured by enzymatic immunoassay using specific antibodies against collagen I and collagen III.

3. The method according to claim 1, wherein the neutral protease is thermolysin or a neutral protease derived from *Clostridium* sp.

4. The method according to claim 3, wherein the degrading-enzyme composition contains thermolysin 0.3 mg/10 ml, collagenase G 2 mg/10 ml and collagenase H 1.1 mg/10 ml.

5. The method according to claim 3, wherein the degrading-enzyme composition contains thermolysin 0.3 mg/10 ml, collagenase G 8.4 mg/10 ml and collagenase H 2.9 mg/10 ml.

6. The method according to claim 1, wherein the degrading-enzyme composition contains a neutral protease derived from *Clostridium* sp., as the neutral protease, and a protease having an α-N-benzoyl-L-arginine ethyl ester hydrochloride (BAEE) degradation activity, as the protease derived from the *Clostridium* sp.

* * * * *

UNITED STATES PATENT AND TRADEMARK OFFICE
CERTIFICATE OF CORRECTION

PATENT NO. : 10,870,833 B2  
APPLICATION NO. : 16/109242  
DATED : December 22, 2020  
INVENTOR(S) : Masafumi Goto et al.

Page 1 of 1

It is certified that error appears in the above-identified patent and that said Letters Patent is hereby corrected as shown below:

On the Title Page (73) Assignees:  
"MEUI SEIKA PHARMA CO., LTD." should read --MEIJI SEIKA PHARMA CO., LTD.--

Signed and Sealed this  
Fourteenth Day of September, 2021

Drew Hirshfeld  
*Performing the Functions and Duties of the*  
*Under Secretary of Commerce for Intellectual Property and*  
*Director of the United States Patent and Trademark Office*